US009903846B2

(12) United States Patent
Bright

(10) Patent No.: US 9,903,846 B2
(45) Date of Patent: Feb. 27, 2018

(54) HYDROCARBON GAS DETECTION DEVICE

(71) Applicant: IBALL INSTRUMENTS LLC, Norman, OK (US)

(72) Inventor: Carl Bright, Harrah, OK (US)

(73) Assignee: IBALL INSTRUMENTS LLC, Norman, OK (US)

( * ) Notice: Subject to any disclaimer, the term of this patent is extended or adjusted under 35 U.S.C. 154(b) by 278 days.

(21) Appl. No.: 14/925,572

(22) Filed: Oct. 28, 2015

(65) Prior Publication Data

US 2016/0047240 A1    Feb. 18, 2016

Related U.S. Application Data

(62) Division of application No. 14/018,987, filed on Sep. 5, 2013, now Pat. No. 9,518,967.

(60) Provisional application No. 61/733,250, filed on Jan. 30, 2013.

(51) Int. Cl.
*G01N 33/00* (2006.01)
*E21B 49/08* (2006.01)

(52) U.S. Cl.
CPC ......... *G01N 33/0006* (2013.01); *E21B 49/08* (2013.01)

(58) Field of Classification Search
CPC ......... G01N 33/0006; G01N 35/00594; G01N 35/00693; E21B 49/08
USPC .............. 73/1.02–1.03, 1.06, 1.07, 23.21
See application file for complete search history.

(56) References Cited

U.S. PATENT DOCUMENTS

| | | | |
|---|---|---|---|
| 7,326,922 B1* | 2/2008 | Mueller | G01N 21/03 250/252.1 |
| 7,379,180 B2 | 5/2008 | Vannuffelen et al. | |
| 7,609,380 B2 | 10/2009 | Vannuffelen et al. | |
| 7,610,142 B1* | 10/2009 | Hoard | F01N 13/008 60/274 |
| 7,823,656 B1 | 11/2010 | Williams | |
| 8,164,050 B2 | 4/2012 | Ford et al. | |
| 8,542,353 B2 | 9/2013 | Christian et al. | |
| 8,586,383 B2* | 11/2013 | Walte | G01N 33/0013 422/83 |
| 8,908,166 B2 | 12/2014 | Matsumoto et al. | |
| 8,912,000 B2 | 12/2014 | Daniel et al. | |
| 2004/0055359 A1* | 3/2004 | Ketler | G01N 33/0006 73/1.07 |
| 2010/0031729 A1* | 2/2010 | Holt | G01N 33/0016 73/1.06 |
| 2010/0219960 A1* | 9/2010 | Moe | G01N 33/0032 340/632 |
| 2013/0081445 A1* | 4/2013 | De Coulon | G01N 27/18 73/25.01 |
| 2013/0265566 A1 | 10/2013 | Smith et al. | |
| 2013/0313448 A1 | 11/2013 | Sun et al. | |

* cited by examiner

*Primary Examiner* — Peter Macchiarolo
*Assistant Examiner* — Anthony W Megna Fuentes
(74) *Attorney, Agent, or Firm* — Hall Estill Attorneys at Law; Tyler J. Mantooth

(57) ABSTRACT

A device and associated method can detect hydrocarbon gas with at least a control module having a plurality of different gas detection means housed in a mobile enclosure, the control module configured to activate at least two different gas detection means to provide amounts and types of gases present in a fluid.

19 Claims, 5 Drawing Sheets

HYDROCARBON GAS DETECTION DEVICE

RELATED APPLICATIONS

This application is a divisional of copending U.S. patent application Ser. No. 14/018,987 filed on Sep. 5, 2013 which claims benefit under 35 U.S.C. 119(e) to U.S. Provisional Application Ser. No. 61/733,250 filed on Jan. 30, 2013, the contents of which are hereby incorporated by reference.

SUMMARY

Various embodiments may generally be directed to the detection of multiple different gases in a single sample.

Assorted embodiments configure a device with at least a control module having a plurality of different gas detection means housed in a mobile enclosure and the control module configured to activate at least two different gas detection means to provide amounts and types of gases present in a mixture of different gases.

DETAILED DESCRIPTION

Figure 1:
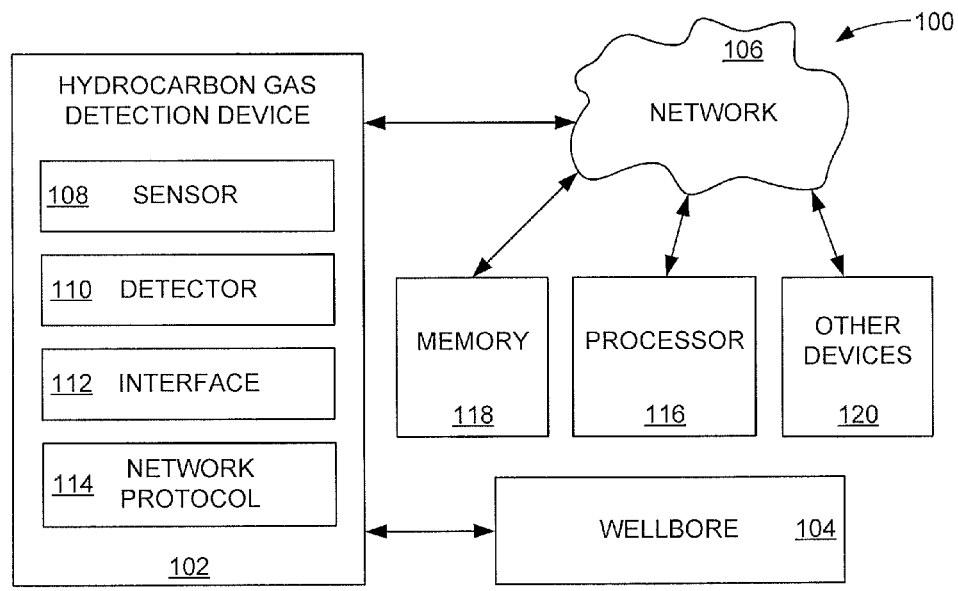
FIG. 1 generally provides a block representation of an example gas detection system in accordance with various embodiments.

The present disclosure generally relates to a device capable of detecting raw natural gasses using a multitude of sensor technologies in the oil and gas field, more particularly in the detection of raw natural gasses during the exploration of oil and gas in a drilling process.

As strata of rock formations are punctured through drilling and fracturing operations, natural gases may be freed and can indicate the composition of rock, volume of hydrocarbons, and effectiveness of hydrocarbon extraction. Such freed natural gases are often pressed into and trapped within drilling "mud" that is pumped at high pressure through the center of a drill string to cool and lubricate the drilling bit as it cuts through earth and rock. After passing through the drill bit, the mud can make its way back to the surface between the drill pipe and the hole outside the drill string while entrapping freed natural gases due at least to the density of the mud compared to the gases. The trapping of natural gases may further occur while the mud is under large pressures and as such the mud will be infused with the various gasses associated with the rocks and earth being fractured. That is, gasses emitted from oil and gas bearing rocks being drilled through are pressed into the mud via large natural and artificial pressures associated with the drilling operations and the depth of the drilling hole.

With the various natural gasses entrapped into the mud, the analysis of the mud can render the constituent gases and concentrations at various depths throughout the drilling hole. In some embodiments, the mud reaching the surface is immediately sent to a filter, such as a screen shaker, to remove the rock cuttings that can individually or collectively be analyzed for solid, liquid, and gas composition to indicate the type and formation of rock being drilled, which may provide verification of geologist's report and hydrocarbon reservoir estimations.

However, accurately separating and measuring the various gasses contained in a mud sample has been challenging and costly due to environmental and equipment limitations can be exacerbated by the addition of the constantly changing characteristics of the drilling mud. For example, drilling mud composites comprised of heavy hydrocarbon based lubricants, such as diesel fuel or crude oil, can be difficult to separate and measure with respect to the mud. In addition, the raw natural gas may be released from the ground with around 90% to 95% methane composition with more complex gasses in concentrations of 5% or less with few exceptions.

While tools exist that are capable of measuring the composition of gases that may emanate from a drilling bore such as a chromatograph and mass spectrometer, such equipment are not designed to operate concurrently on a single sample, survive harsh operating environments, be easily transported, or provide precise measurements in field conditions found on a drill site. For instance, a laboratory grade chromatograph, while a highly accurate tool, has not been adapted to the problematic electrical systems often found in drilling environments or reduced in size to allow physically robust casings, which will quickly degrade a typical laboratory grade chromatograph system into uselessness at a well site.

Further issues can plague field use of laboratory grade chromatograph systems as daily and sometimes hourly recalibrations are necessary to provide reliable measurements. The use of a chromatograph may include column chemicals that are hygroscopic, which poses a number of accuracy difficulties in oil field use as water is absorbed into the column chemicals making them useless over time for measuring well samples that often have both high levels of water vapor and oxygen. Laboratory grade chromatographs may also require a specific column temperature to be maintained within a very tight temperature range to garner repeatability and accuracy.

Even with the various issues in measuring a gas sample using a chromatograph, the precision of the instrument often is not reliable enough to discern different hydrocarbons, such as between Methane (C1) and Ethane (C2), as the Methane to Ethane ratio may be too large, such as a 90 to 1 ratio, and the gasses are so close in molecular weight that most if not all chromatographs have trouble returning to a baseline separation of these two gasses. Some chromatographs require large and heavy tanks of travel gas such as Hydrogen or Helium and in the case of flame ionization detector (FID), or other flame photometers, a special heavy and bulky FID fuel gas tank is required, which impedes the ability to transport, set-up, and administer a series of reliable tests as the instrument becomes useless if any of these tank gasses run empty.

With these issues in mind, various embodiments may generally be directed to a gas detecting device capable of utilizing multiple sensors and sensor technologies according to various predetermined logical algorithms to detect the types and amounts of gases present in a single sample. For instance, a gas detecting device may have at least a control module having a plurality of different gas detection means housed in a mobile enclosure with the control module configured to activate at least two different gas detection means to provide amounts and types of gases present in a mixture of different gasses. The ability to monitor, modify, and control a variety of different gas detecting means according to a logical algorithm can allow for efficient adaptation of the gas measuring process to account for diverse and variable conditions, such as ambient temperature, barometric pressure, and humidity. The automation and varying control of multiple gas detectors may further allow for a concise physical device constructed that is robust to vibration, weather, electrical supply, transportation, abnormalities, and calibration.

FIG. 1 generally provides a block representation of an example gas detection system 100 configured in accordance with various embodiments to detect the types and amounts of gases in a single sample. The system 100 has a hydrocarbon gas detection device 102 connected to a wellbore 104 and a network 106. Such position of the gas detection device 102 allows various aspects of the device 102 to engage assorted portions of the wellbore 104 while connecting to and communicating with any number of remote nodes to download and upload data, compute gas detection algorithms, and operate in conjunction with other devices.

In the non-limiting example of FIG. 1, the hydrocarbon gas detection device 102 is constructed with at least a sensor 108 and detector 110 that can be utilized concurrently and independently to identify environmental and testing fluids that have entrapped gasses from the wellbore 104 recently after fluid has been evacuated from the wellbore 104, such as less than five minutes after evacuation. The gas detection device 102 may further have one or more interfaces 112 that communicate with a user and peripheral devices while enabling a network protocol 114 to establish, maintain, and service the transfer of data across the network 106. These gas detection device 102 components are not required or limiting, but can allow for data to be remotely computed via at least one processor 116, stored in a remote memory 118, and combined with data from other devices 120, such as other environmental, mechanical, and hydrocarbon detection equipment.

Figure 2:
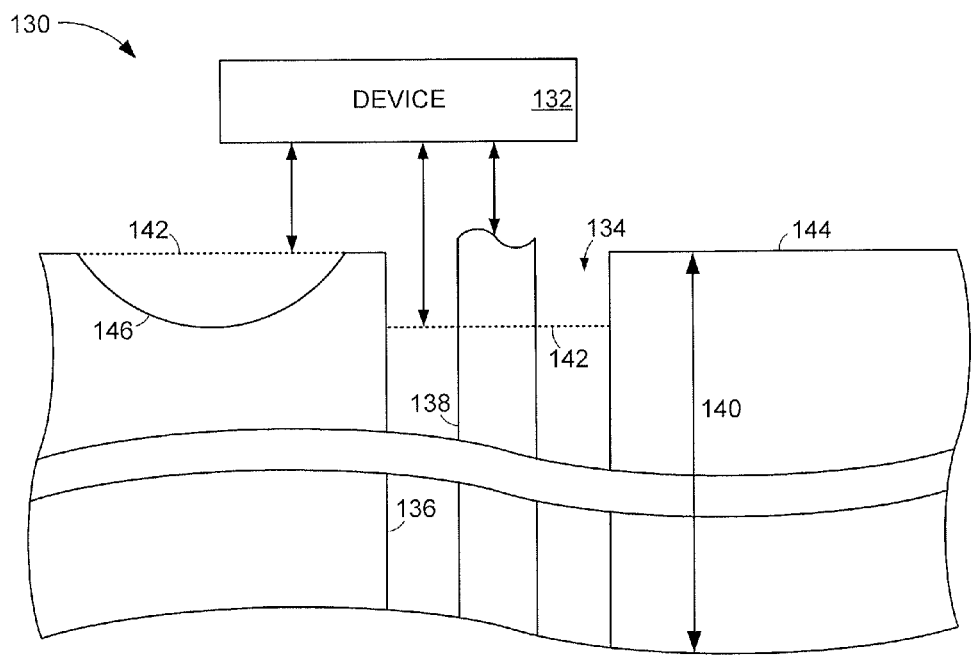
FIG. 2 displays a block representation of an example gas detection environment utilized in accordance with some embodiments.

It can be appreciated from FIG. 1 that the hydrocarbon gas detection device 102 can be utilized in a variety of different manners and environments where hydrocarbons are present. FIG. 2 displays a block representation of a portion of an example hydrocarbon environment 130 in which a hydrocarbon gas detection device can be employed in accordance with some embodiments. As shown, at least one hydrocarbon gas detection device 132 can be positioned outside a wellbore 134, which is constructed with a wellbore sidewall 136 and drilling piping 138, such as casing and rotating drilling pipe, positioned therein.

It is to be understood that the wellbore 134 can be any depth 140 and have constant or varying amounts of drilling fluid 142, such as drilling mud, stagnant or flowing below the ground surface 144. The gas detection device 132 can be configured to engage and measure the amount of gas present in any location within the wellbore 134, such as outside and inside the drilling piping 138. Such engagement is not restricted to a particular type or size of probe, sensor, or receptacle and can measure drilling fluid that has gas, liquid, and solids individually and together by contacting a sample. In assorted embodiments, the gas detection device 132 removes a drilling fluid sample from the wellbore 134 or from a fluid retaining structure 146, such as a mud pit, and analyzes the sample in a controlled environment. However, other embodiments conduct some or all of the drilling fluid analysis while the fluid is resident in its native location, such as the wellbore 134 and retaining structure 146.

With the ability to engage drilling fluid 142 at different locations in and around a wellbore 134, the gas detection device 132 can measure the drilling fluid 142 under diverse conditions that allows for increased gas detection accuracy. For example, drilling fluid 142 readings can be compared between downhole measurements and controlled environment measurements to ensure gas types and amounts were not lost during transport. It should be noted that the controlled environment in which drilling fluid 142 is measured external to the wellbore 134 and retaining structure 146 can be any size and duration with one or more conditions being controlled, such as pressure, temperature, light, humidity, and fluid density.

Figure 3:
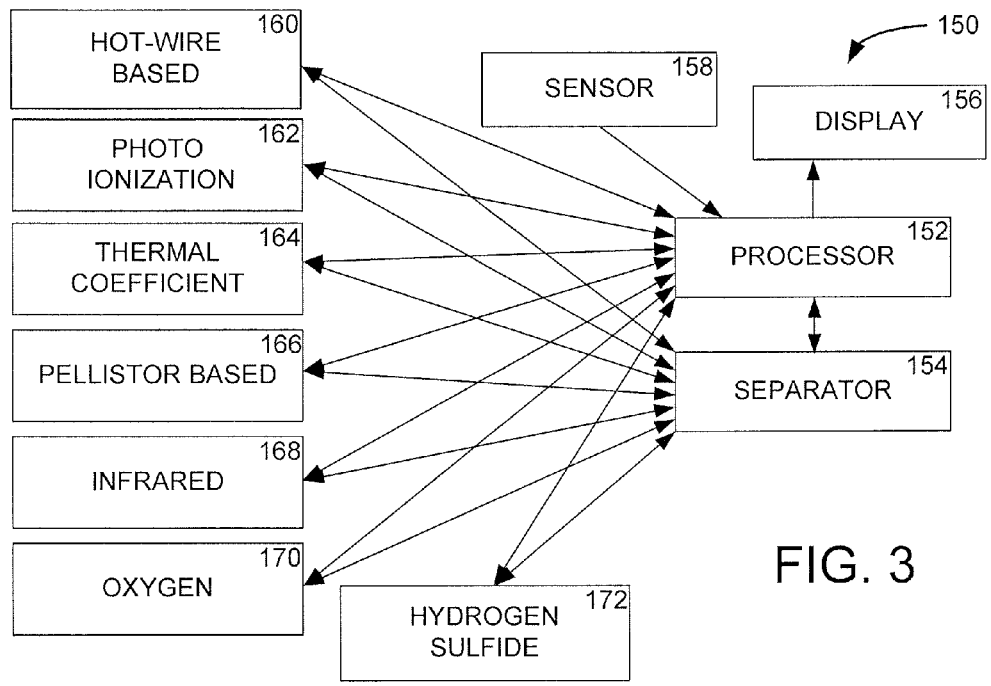
FIG. 3 shows a block representation of an example gas detection device capable of being used in the example system of FIG. 1 and environment of FIG. 2.

While a gas detection device may be configured with any number of components to be used in a wide variety of environments, FIG. 3 provides a block representation of an example gas detection device 150 that can efficiently and reliably measure a single sample and detect the types and volumes of constituent gases. The gas detection device 150 has a processor 152 that can be a part of a computing system that stores data in memory, runs software, and communicates over a network via appropriate protocol. The processor 152 can be configured to control at least a gas separator 154, electronic display 156, various sensors 158, and one or more gas detector means to take a gas sample and conduct testing in accordance with a locally or remotely stored logical algorithm to discern the various gases that make-up the sample.

Among the unlimited variety of detection equipment capable of being controlled by the processor 152, a hot-wire based detector 160, photo ionization detector 162, thermal coefficient detector 164, pellistor based detector 166, infrared detector 168, oxygen detector 170, and hydrogen sulfide detector 172 may be used individually, sequentially, or concurrently to analyze a sample. With past incarnations of the hot-wire 160 and pellistor 166 based detectors, the detector would become carbonized or burn out with too much methane or raw natural gas being present in the detector chamber. The previous use of an infrared detector 168 for hydrocarbon measurement was attempted but discontinued due to the fact that infrared detection varied wildly with temperature and the different gasses found in the drilling fluid.

Even with gas detection instruments like the Bloodhound System made by iBall Instruments of Edmond, Okla., infrared detectors can be inefficient, on its own, as the detection systems have to adaptively learn the reactivity of the gasses and adjust the infrared detectors on the fly. With the gas detection device 150 shown in FIG. 3, the processor 152 can utilize any of the various detectors in accordance with the predetermined logical algorithm in order to provide the most accurate and efficient gas measurement. In some embodiments, the processor 152 can choose or adapt the logical algorithm in response to readings from one or more sensors 158, which allows the algorithm to activate the best possible detector to provide the most accurate measurement given the sensed conditions.

The gas detection device 150 is not limited to the configuration, connections, and equipment provided in FIG. 3, as any number of similar and dissimilar detectors and detection technologies can be cooperatively utilized individually, sequentially, and concurrently to provide monitored and automated testing of a sample to better gauge the absolute value of the raw natural gasses in the sample. The ability to utilize more than one detector of a single type provides redundancy to the device 150 that can be utilized for optimized accuracy and device reliability in the field. Additionally, the multitude of different gas detecting technologies combined with the ability to switch between totally separate types of gas detectors allows the device 150 to adapt to changing conditions, such as measure environmental conditions from the sensor 158 and damage to a plurality of detectors. In the event damage is detected, the device 150 can logically disconnect the failed or damaged sensors and continue operating one or more other detectors, in some embodiments.

As an example of the characteristics of gas detectors that can be selected by the processor 152, the hot-wire based detector 160 can be activated to efficiently detect low levels of natural gas, but would be damaged when higher levels of gas are detected. Hence, the processor 152 can deactivate the hot-wire based detector 160 at a predetermined threshold, such as an elevated temperature or pressure, and start utilizing another detector like the infrared detector 168 or the thermal coefficient detector 164 for high level detections. The gas detection device 150 may further be responsive to extremely low natural gas levels, in which the photo ionization sensor 162 could be initially utilized instead of the hot-wire based detector 160.

In some embodiments, more than one detector of each type are included into the device 150 to provide alternatives for the processor 152 such as when a detector is being calibrated or cleaned. Also, the miniaturization of electronics can allow for such redundant detectors without increasing the physical size of the device 150 to the point where it is not portable. Such reduced physical size of computing components is complemented by the increased computing power of such components to allow seamless, automatic, and unnoticed device 150 testing.

Figure 4:
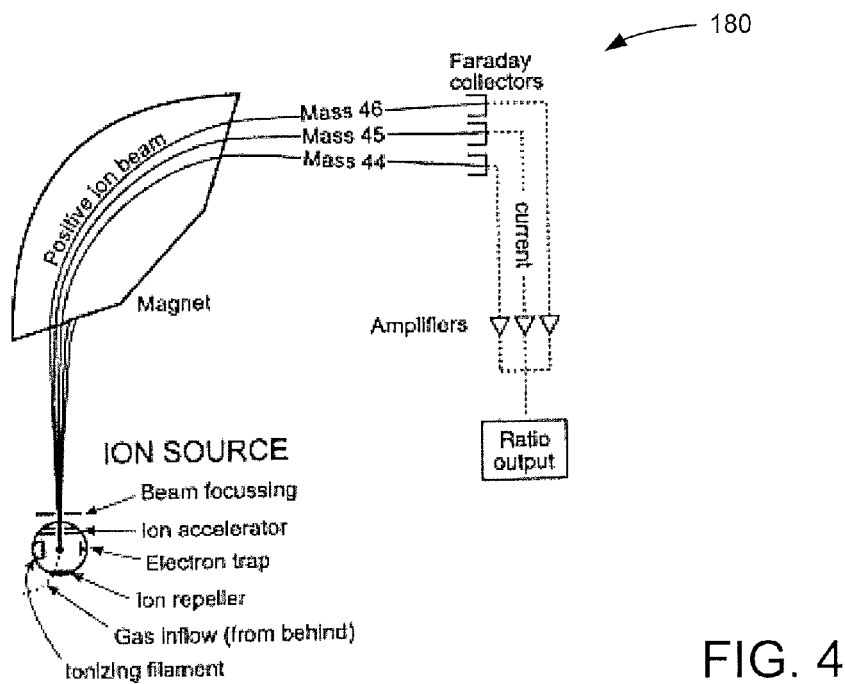
FIG. 4 is a block representation of an example gas detector capable of being used in the example gas detection device of FIG. 3.

FIG. 4 generally illustrates a block representation of an example mass spectrometer 180 that may be used in the gas detection system 100 of FIG. 1, in the gas detection environment 130 of FIG. 2, and with the gas detection device 150 of FIG. 3 in accordance with assorted embodiments. The mass spectrometer 180 can, in various embodiments, be used at an oil well site, but may have significant operational and structural disadvantages in their present construction. Compared to a chromatograph that uses a chemical column based means of gas separation, the mass spectrometer 180 uses the principal of ionizing the sample gas and injecting it into a high vacuum field across a very high magnetic field. The charged particles are then deflected by the field to a different vector of travel and thereby striking isolated plates causing the electrically charged particle to transfer the charge to the isolated plates. In theory, the charged plate is then amplified to give a respective output of the gas stream of charged particles, which should give results almost instantly of all gasses that are monitored.

In practice, a mass spectrometer 180 is not practical field equipment due at least to gain block, large vacuum chamber needed to test, operational temperature, and multiple sources of contamination. With a first gain block that may be over a billion, the tiniest change in temperature or electrical deviation can cause large unpredictable results. For instance, a chamber vacuum that is almost an absolute vacuum can contaminate the chamber with normal air particles that become charged and degrade the accuracy and sensitivity of all the readings. Contamination of the vacuum chamber and electrical aspects, such as a PC board, of the mass spectrometer 180 with any debris or materials will cause deviations as the material on the high-gain feedback resistors cause large drifts.

The use of a mass spectrometer 180 is not required or limiting, but can be used in various embodiments to provide gas measurements, such as in low environmental contamination sites or with other chemical gas separations. Since the natural gasses being tested are themselves reactive to chemical compounds, there are ways to chemically isolate the gasses such as taking rock samples, or cuttings, to a laboratory to be crushed and analyzed. Analyzing gasses contained in rock cuttings can involve placing them into a vacuum chamber where the gasses can be pulled out under high vacuum and heat and then pulled through a laboratory grade chromatograph. The removal of rock cuttings from drilling mud can allow for the chromatograph to be used in a laboratory environment, which increases reliability and accuracy of the results, if conducted properly.

However, the excavation of rock cuttings can lack the breadth and timing of an on-site gas analysis from drilling mud as gases escape from the rock during transportation to the laboratory. While air tight containers may be used to reduce gas leakage, accurate testing of escaped gases after the delay of transportation is not as accurate as on-site testing. Hence, an on-site testing of drilling mud for natural gases entrapped therein can provide a more precise and accurate real-time perception of the type and yield of the hydrocarbon reservoir being drilled.

The utilization of one or more gas detectors, such as the infrared detector 168 of FIG. 3 and the mass spectrometer 180 of FIG. 4, with a logical algorithm and the ability to adapt to sensed conditions both environmentally and with the sample can provide more accurate on-site gas measurements, but the separation of gas from the drilling mud that often contains a variety of heavy, light, and aromatic materials like diesel fuel can be difficult without losing a portion of the entrapped raw natural gases. It has long been known that if an object is immersed in a liquid, that object will displace a volume of liquid equivalent to its own volume. By comparing the weight of the object and the weight of this displaced volume of liquid, you can determine if the object will float or sink.

When a balloon is filled with something other than air and then released into air, it will float or sink based on the same principle. If the weight of the volume of air displaced by the balloon is less than the weight of the balloon and the gas inside, the balloon will drop to the ground. If the weight of the air displaced by the balloon is greater than the weight of the balloon and the gas inside, the balloon will float upwards. This force, or buoyancy, either positive or negative, is exactly the difference in the weight of the balloon and its contents, versus the weight of the volume of air displaced. This is the principal behind the Specific Gravity of a material.

In principal, the gasses we breathe are made up of nitrogen ($N^2$), oxygen ($O^2$), and many other gasses that do not bond together but are constantly being mixed up in our atmosphere with very similar molecular weights. Breathable air constituent gases do not generally separate but are happy just sitting together in a constant atmospheric soup. In contrast, natural gas comes from the ground and is primarily Methane and lower concentrations of other gasses, as provided in Table 1.

TABLE 1

| General Raw Natural Gas | Concentration |
|---|---|
| Methane (CH4) | 70%-90% |
| Ethane (C2H6) | 5%-15% |
| Propane (C3H8) | <5% |
| Normal butane (n-C4H10) | Balance |
| Isobutane (i-C4H10) | Balance |
| Pentanes C5H12 | Balance |
| CO2 | Balance |
| H2S | Balance |

With raw natural gas containing known gases that have a specific gravity that can be physically separated via mechanical separation, such as with a centrifuge, may be used in some embodiments to aid in the time, sensitivity, and accuracy of gas detection with the device 150 of FIG. 3.

Figure 5A:
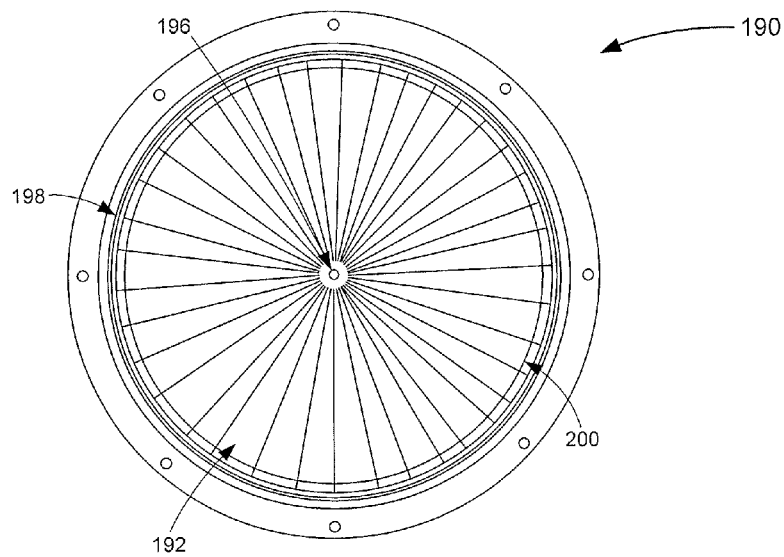
FIGS. 5A and 5B respectively illustrate top and exploded side views of an example gas separator configured in accordance with various embodiments.
Figure 5B:
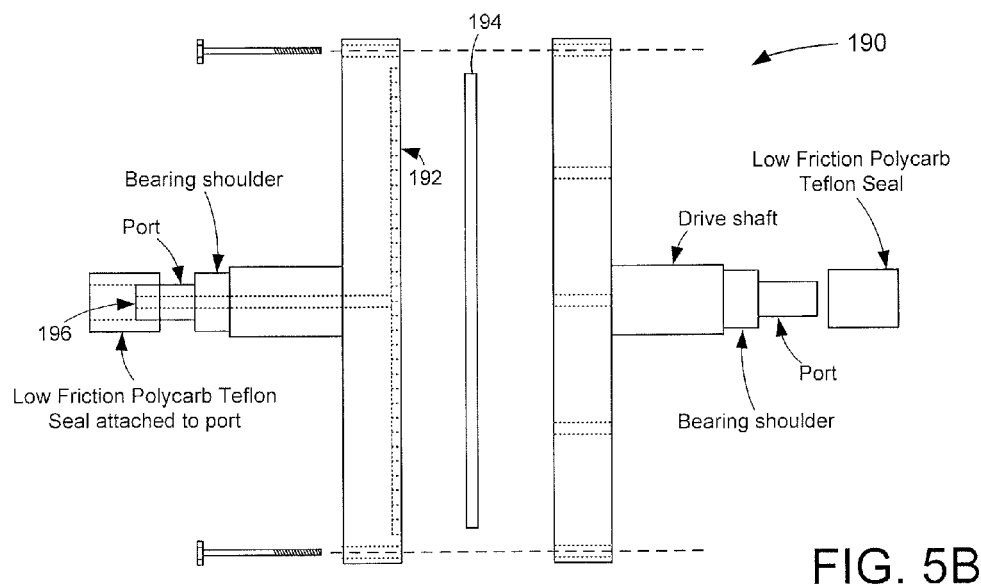

As shown in FIGS. 5A and 5B, a gas centrifuge 190 can be adapted to facilitate hydrocarbon separation and testing that provides accurate results in less than two (2) minutes and in some situations less than thirty (30) seconds. Extracted gasses from the mechanical extractor located at a shaker, such as a possum belly or spoil separator, can contain a plethora of diverse materials from pure air to almost pure diesel to crude oil fumes. The raw natural gas that needs to be separated and quantified is trapped within as only a small part of the overall extracted gas as the diesel and other heavy hydrocarbon fumes can overpower and overtake most current hot wire or pellistor based detector systems forcing most systems that use petroleum based drilling mud to heavily dilute the incoming sample with air, which is known as air dilution. In doing so, the sample to be analyzed has also been diluted at a predetermined ratio like 10:1 or more. Such air dilution reduces the effectiveness of a gas centrifuge as constituent gas portions are reduced and makes accurate gas measurements difficult.

The use of infrared gas detectors may be used in various embodiments with the gas centrifuge 190 to measure high background gasses without overwhelming the equipment with undiluted air. As shown in Table 2, the gasses expected from raw natural gasses have specific gravity levels from 0.55 to 2.9 while other heavy hydrocarbons have been omitted that would be typical in the hydrocarbon based drilling mud.

TABLE 2

| General Natural Gas | Specific Gravity |
|---|---|
| Air reference (20.9% O2, 78% N2) | 1.0000 |
| Hydrogen | 0.0696 |
| Helium | 0.1380 |
| Methane | 0.5537 |
| Nitrogen | 0.9669 |
| Ethane | 1.0378 |
| Oxygen | 1.1044 |
| Carbon Dioxide | 1.5189 |
| Propane | 1.5219 |
| n-butane | 1.9400 |
| iso-butane | 1.9400 |
| Pentane | 2.4870 |
| Hexane | 2.9730 |
| Heptanes | 3.4590 |
| Octane | 3.9440 |

Each of these gases have a specific gravity level that is much greater than air, which allow a centrifugal separation to be effective.

While not required or limiting separation of gases with a centrifuge would start in various embodiments with a chamber flush that consists of pushing air into and out of the chamber 192 to flush any hydrocarbons that are remaining in the chamber 192. Next, the sample gasses would be pushed into the chamber 192 where they would be turned at a predetermined speed inside the centrifuge 190, such as 8000, 12000, and 15000 RPM. Inside the centrifuge 190 the gasses are separated into bands of gas according to their respective specific gravities. The centrifuge 190 would be capable of separating gasses with differences in specific gravity greater than 0.2 units, as provided in Table 2.

The gasses are subsequently drawn slowly out of the chamber 192 and across a sensitive detector where each band is detected and quantified. It is of note that since the output is from a centrifuge, instead of a chromatograph, both time and amplitude can be used to quantify the gas measurements. The wider the band based on time, the amount of gas per sample, and the amplitude of the gas can dictate which band it has come from to aid the sensitive detector in identifying gases due to the sensitive detector having predictable output reaction to different types of gas.

In some embodiments of device 150 of FIG. 3, the centrifuge is configured with a chamber 192 measuring approximately 4" diameter that will have to turn at around 8000 RPM. Based on the general principal of rotational G force calculations of:

$$G\ (RCF) = 0.00001118 \times \text{Radius in cm} \times RPM^2 \qquad \text{Equation 1}$$

With a rotational speed of 8000 RPM, the G force for a 2 inch chamber 152 is 18,174 G and 36,348 G for a 4 inch chamber 192. Such force should provide acceptable separations within a few seconds.

The use of such force may be effective and efficient, but can be easily undone if the separated gases remix as they are drawn from the chamber 192. Any internal turbulence may cause the stacked and now separated gas column to collapse and the gases to once again intermingle. Accordingly, a predetermined artificial gravity can be induced by maintaining the centrifuge 190 at a reduced, above zero, speed, such as 500 RPM, to prevent gas remixing while gases are drawn from the chamber 192 and measured.

Along with gas remixing, turbulence may occur within the chamber 192 and the lines transporting the gases to a detector. Excessive turbulence could cause the gasses to intermingle and ruin the separation and detection process. To keep turbulence to a minimum, a septum disk 194 should be chamfered at the edge and the transition points smoothed to ensure laminar flow of gases during extraction. Such laminar flow may further be controlled by gradually starting the vacuum extraction system, which can easily be done with accurate and precise control of the draw vacuum that has the separated gasses pulled from the center of the centrifuge 190.

FIG. 5A illustrates a top view of a portion of the gas centrifuge 190 with a plurality of chambers 192 radially extending from an inlet aperture 196. As shown in the exploded side view of FIG. 5B, the gas centrifuge 190 can be constructed of two joining disks respectively configured with chambers 192 and outlet veins on opposite sides of the septum disk 194. The outlet veins can be constructed with a predetermined diameter and positioned at predetermined locations to allow a particular volume of gas to be extracted either while spinning or during controlled vacuum pressure.

The separate centrifuge components may be sealed by a sealing feature, such as an O-ring resting in a groove 198 continually extending around the various chambers 192. A ridge 200 may further be included in each chamber 192 to align the septum disk 194 and maintain position during operation. With the non-limiting embodiment shown in FIGS. 5A and 5B, the centrifuge 190 is designed as a horizontal fixture that holds tapered sealed Timken bearings and weighs less than ten (10) pounds, which facilitates mobility for drilling site use.

Figure 6:
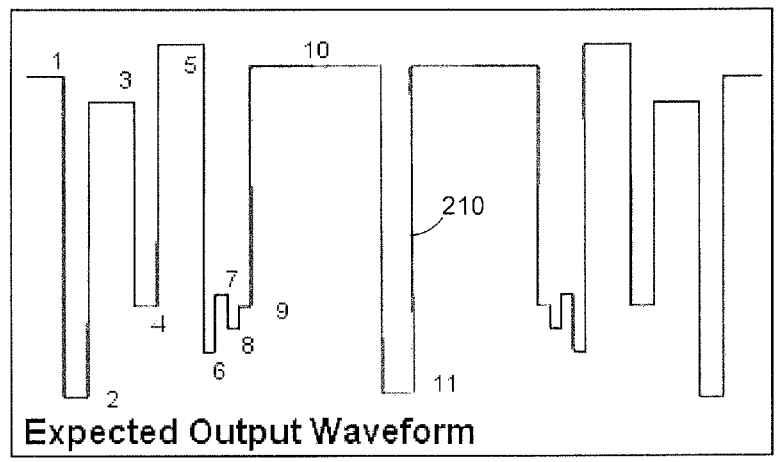
FIG. 6 plots example operational data associated with a gas detection device.

Through the various embodiments of the present disclosure, hardware has been generally illustrated that is capable of rendering separate gases and testing those gases for volume. While the hardware can provide efficient separation, control of the various gas detectors, separator speed, and adapting to environmental and operational conditions can make the difference between accurate and unreliable test results. FIG. 6 graphs an expected output waveform 210 resulting from operation of a gas detection device, such as device 150 of FIG. 3, according to a predetermined logical algorithm (PLA).

The PLA is the logics in which the intelligence and automation of a gas separation device combines to control sensors within the device itself and make changes to its logistical algorithm on the fly. That is, the multitude of the same type of sensor as well as a multitude of different types of sensors can be logically controlled by the PLA to ascertain the amounts of the varied and different types of gasses within the collected sample itself while also having the ability to self-correct for errors.

As a non-limiting example of the PLA, a gas detection device is assumed to have an infrared detector known to be more accurate at greater than 5% methane, a pellistor based detector known to be more accurate at less than 5% methane, an oxygen detector that does not detect or react to methane or its variants. Such an example gas detection device can simultaneously compare readings from all three detectors and making the following logical considerations:

(1) if the Oxygen sensor is at 20.9% (100% room air) then
   (a) the infrared sensor should show 0% methane
   (b) the pellistor sensor should show 0% methane
(2) if the Oxygen sensor is at 19.5% then
   (a) the infrared sensor should show 5% methane
   (b) the pellistor sensor should show 5% methane
(3) if the Oxygen sensor is at 10.45% then
   (a) the infrared sensor should show 50% methane
   (b) the pellistor sensor should be shut off to prevent damage
(4) if the Oxygen sensor is at 0.1% then
   (a) the infrared sensor should show almost 100% methane
   (b) the pellistor sensor should be shut off to prevent damage The logics stand to reason that the PLA should also consider the inverse findings as well in the same preceding scenario:

(1) if the infrared sensor is at 0% methane then
   (a) the Oxygen sensor should show 20.9% (room air)
   (b) the pellistor sensor should show 0% methane
(2) if the infrared sensor is at 5% methane then
   (a) the Oxygen sensor should show 19.5%
   (b) the pellistor sensor should show 5% methane
(3) if the infrared sensor is at 50% methane then
   (a) the Oxygen sensor should show 10.45%
   (b) the pellistor sensor should be shut off to prevent damage
(4) if the infrared sensor is at almost 100% methane then
   (a) the Oxygen sensor should show about 0.1%
   (b) the pellistor sensor should be shut off to prevent damage Further the PLA has an ability to self-calibrate and correct itself in the following scenario:
(1) The Thermal Coefficient Detector (TCD) is showing 50% methane
(2) The infrared detector is showing 50% methane
(3) The Oxygen sensor is showing 8% Oxygen (should be 10.45%)

Based on the basic principal that the majority of gas detecting technologies will be accurate, the unexplained and unexpected Oxygen sensor technology value will be judged to be inaccurate and thus the PLA will correct this Oxygen calibration point to 50% or (10.4%) in the preceding scenario thereby correcting a calibration point and self-calibrating the Oxygen sensor.

Further the PLA has the ability to detect failed sensors and correct itself in the following scenario:
(1) The Oxygen sensor is showing 10.45% Oxygen (50% room air)
(2) The infrared detector is showing 50% methane
(3) The Thermal Coefficient Detector (TCD) is showing 0% methane;

Based on the basic principal that the majority of sensor technologies will be accurate, the unexplained and unexpected sensor technology value will be judged to have failed due to the great inaccuracy of the TCD output compared to other sensor technologies and thus the PLA will disallow and ignore further reading from this one TCD sensor until corrected and may opt to start watching a back-up TCD sensor.

Overall, with the collection of different gas detectors available to the PLA, the gas detection device can clearly pick and choose between a plurality of technologies, compare all detectors available to it and come to a more accurate output as well as correct for drifting sensors or ignore failed sensors all together in favor of backup sensors, or other good detectors with more expected outputs.

Further, the PLA, upon its final calculations may also opt to average all, some or one of the detector's measurements and then output the calculated real natural gas outputs. The PLA also has the option to monitor the temperature of the various detectors, and the humidity of the sample gasses which can have a large effect upon the reactivity of the gasses upon the sensors. When taking into effect the temperature and humidity of the sample gasses, the PLA can also opt to correct the calculations from each sensor and automatically compensate for any known drifting due to such temperature and/or humidity changes in the sample.

One issue in the examination of drilling mud can be that some drilling fluids are based primarily on diesel fuel, raw crude oil, or other volatile chemicals instead of water. In such a case, some detection equipment technologies can react to the fumes created by these organic drilling fluids and indicate methane where there is little or no methane at all. In this case the PLA can re-calibrate for the volatile organic drilling fluid fumes since some of the detectors within the device do not react to these organic fumes, such as the Oxygen and Hydrogen Sulfide detectors. More to the point, if the operator notifies the PLA that the drilling fluid is not water based, then the PLA can proactively re-calibrate to compensate for the known fumes.

The PLA, when notified by the user that the drilling fluid is not water based, can also opt to change the voltages upon the pellistor and hot-wire or pellistor based detectors. It is not commonly known that one can reduce the voltage on these types of sensors and such heavy hydrocarbon fumes will cease to react to the catalyst that these sensors are built upon. Thus, the PLA can correct for organic fumes in this way as well. The PLA can also control the temperature of an individual or collective set of detectors. It is not well known that different sensors react differently at different static temperatures. To reduce the inaccuracy of the collection of sensors, the PLA can monitor and maintain all or some sensors to a known temperature thereby eliminating a major source of sensor errors.

Figure 7:
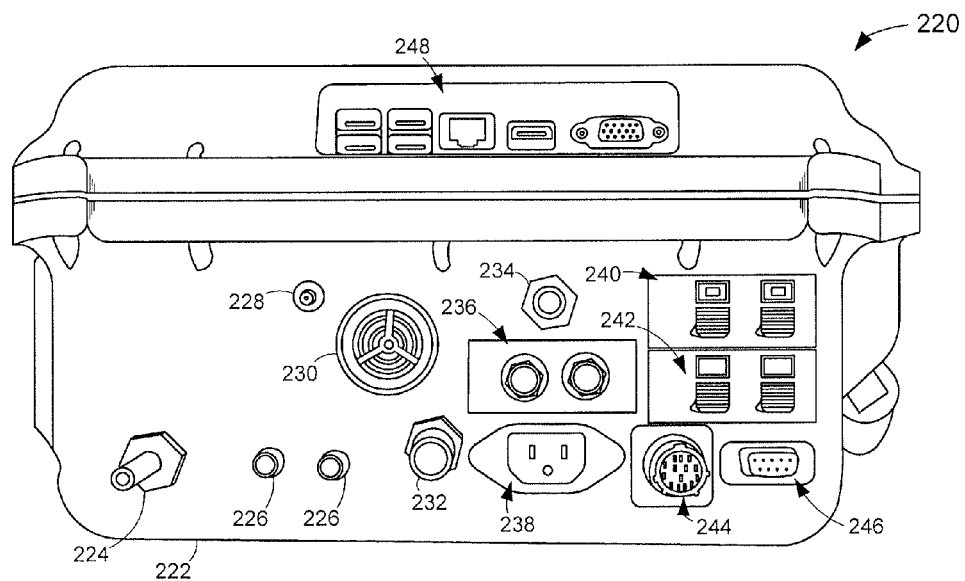
FIG. 7 displays a perspective side view of an example portable gas detection device constructed in accordance with some embodiments.

While the PLA can be implemented in a variety of gas detection devices, FIG. 7 displays an example portion of an example gas detection device 220 configured in accordance with various embodiments. The placement of various gas, electrical, and computer connectors on a portable gas detection device can be problematic in that the connectors are harder to get to in order to service the portable gas detection device and said connectors. As shown by the gas detection device 220 of FIG. 7, placement of all gas inlets and outlets on the external left side surface of the device case 222 can provide efficient access, service, and function catered to drilling field site operations and specific system function, like the Bloodhound™ system by iBall Instruments.

While the specific location, connection, type of connection, and function of the various inlets and outlets of the gas detection device 220 are not limited to the configuration shown in FIG. 7, various embodiments position include at least a sample line inlet port 224, case vent 226, GPRS (or) CDPD external radio antenna connection 228, Sonalert audible alarm device 230, sample line exhaust port 232, electrical breaker for DC input/output port 234, direct current input/output port 236, main AC power input port 238, geolograph switch input 240, pump stroke switch(es) input 242, Pason Military style RS422 external WITS interface 244, and DB9 external WITS interface 246 connections.

More specifically, various embodiments may configure the sample gas inlet 224 with a smaller ¼" hose barb connection on the side is for the sample gas in. Right before this connector, there can be a line filter and a water catch canister (dropout jar). The filter is to remove particulate materials and contaminates that may clog up the sample line inlet port and damage the instrument. All the sample line connections should be attached firmly using some type of hose clamp. The catch canister should be rated for a minimum of 150 PSI. These ratings may correspond because the Bloodhound™ system will automatically attempt to clear a blocked sample line with sudden positive pressures between 50 PSI and 110 PSI when in a sneeze or blowback mode of operation.

The case vents 226 are two small ports that allow the device 220 to regulate and monitor atmospheric pressures and also allow device 220 to maintain internal pressure equilibrium. Meanwhile, the GPRS or CDPD Cellular Network Radio Connection 228 can be a SMA antenna connection for the wireless GPRS or CDPD internet connectivity. Normally, a 5 dB gain magnetic mount antenna is connected here. This radio connection allows the device 220 to connect to other devices, such as devices 120 of FIG. 1 for reception of data. This is only one communications link that allow device 220 connection to the network to allow remote technicians to control, diagnose, adjust, reprogram, or maintain the device 220.

Below the radio connection, an audible alarm module 230 is positioned. This alarm will sound when the device 220 detects a problem with the system or one of the parameters it is monitoring goes into alarm state. The sample gas exhaust port 232 is a ½" hose barb connection. This larger size exhaust hose keeps the system from developing a back pressure or getting plugged with ice during cold weather. It may be disadvantageous to plug the exhaust line or use a smaller ¼" hose because exhaust line back pressure may increase and the system may not operate correctly.

With the electrical components of the gas detection device 220, the electrical breaker 234 can provide protection as it will be tripped if the incoming or outgoing amperage is over a predetermined threshold, such as 8 amps or above. When the breaker 234 is tripped, the white round poppet will not be flush with the housing. To reset the breaker just push the white round poppet back into the housing until it is flush. The device 220 DC power port 236 allows the user to either power the device 220 from an external 12 VDC source such as a vehicle, or to power an external DC Cavitator extractor system from the internal power supply. The DC port has overload, spike, sag and transient protection built in. If powering the device 220 from a DC power port from an automobile, the power port 236 can be configured to indicate an incorrect polarity being used, which can cause a fuse in the automotive system to open. As an added feature, and with the correct adapter, this 12 volt DC power port can operate a variety of different automotive appliances, such as a cell phone charger, GPS, and a mobile computer. Various embodiments limit the output current from the power port 236 to 8 amperes by a breaker.

Below the DC port is the universal AC power input 238. This AC input can handle from 90-260 volts AC and from 43-68 hertz (Hz) (or) up to 300 VDC but may be modified without limitation to allow overseas operation on 240 volts, 50 Hz as well as 120 volts, 60 Hz operation. The upper red and black spring terminal clamps are for the geolograph switch input 240. In drilling environments that are not WITS or WITSML compliant, the most common method to transmit drilling foot changes, other than WITS, is with a switch connected in some manner to a mechanical geolograph. As more drilling rigs become WITS and WITSML compliant, this should be less common. The lower red and black spring terminal clamps are for the pump stroke(s) switch input 242. Connecting a switch or inductive sensor to the armature of the drilling pump and then running the switch lines to this input will automatically allow the device 220 to monitor switch induced pump strokes. If there is more than one drilling pump, multiple pumps can be monitored by running the switches in parallel.

In order to communicate to the Pason Electronic Drilling Recorder (EDR) system without the burden of any external hardware, the gas detection device 220 can be configured with a Pason compatible RS422 connection interface 244 into the device 220. This allows for direct connection to the Pason EDR system to obtain duplex WITS communication and information. Generally, no user intervention is necessary on the device 220 to access the Pason WITS information when using this connection. After connecting the 10 pin round military type cabling to the device 220 from the Pason EDR system, the device 220 can automatically establish communications with the Pason system and start acquiring and sending WITS data.

If the drilling rig has a TOTCO, EPOCH or other drilling system, then the communications from the drilling computer to the device 220 may come from a different source. If connecting the device 220 to a TOTCO system, a TOTCO technician might have to come to the drilling site and hook up a secondary computer. This computer talks to the rig and makes available the WITS information through a 9 pin null modem cable to the device's 9 pin WITS port 246. If connecting to an EPOCH system, the WITS data comes from a box called a Device Extender, which allows for depth pulses, pump pulses, and on bottom marking. In accordance with assorted embodiments, the device 220 has one or more serial ports for WITS data. Connecting the device's 9 pin male WITS connector through a null modem cable to the EPOCH system, COM 1, allows serial data transfer to and from the device 220.

Along with the gas inlet/outlet and testing controls provided on the lower half of the device case 222, a plurality of computer inputs 248 may be positioned on an opposite top half of the device case 222. The plurality of computer inputs 248 may have at least RJ45 connector to hook into a local Ethernet network and operates using DHCP (Dynamic Host Configuration Protocol) services. This Ethernet connection can be tied into the Internet as well as to other devices. If so, the device 220 can utilize such a connection to communicate with a remote server, such as an iBall Instruments server system. The plurality of computer inputs 248 may further have 4 user accessible USB connections that are rated for USB 2.0 speeds or greater. A large number of external devices can be connected into the device 220 for ease of use by the system user. If the device 220 is to be used locally, the user will need to supply a monitor of their choice. The monitor will need to connect to the VGA connector, which is efficiently incorporated into the plurality of computer inputs 248.

It can be appreciated that the consolidation of electronics into the mobile device case 222, which may weigh less than 100 pounds in assorted embodiments, can allow for the testing of fluids and communication of testing results in a variety of different manners. For instance, fluid measurements taken by one or more gas detectors can be logged and computed by a computer connected to the gas detection device via computer inputs 248 before gas types and amounts are communicated to a remote destination via the radio antenna 228. Other embodiments utilize the various peripheral inputs, like interface 244 and WITS port 246, to facilitate fluid testing and communicate fluid test results.

Figure 8:
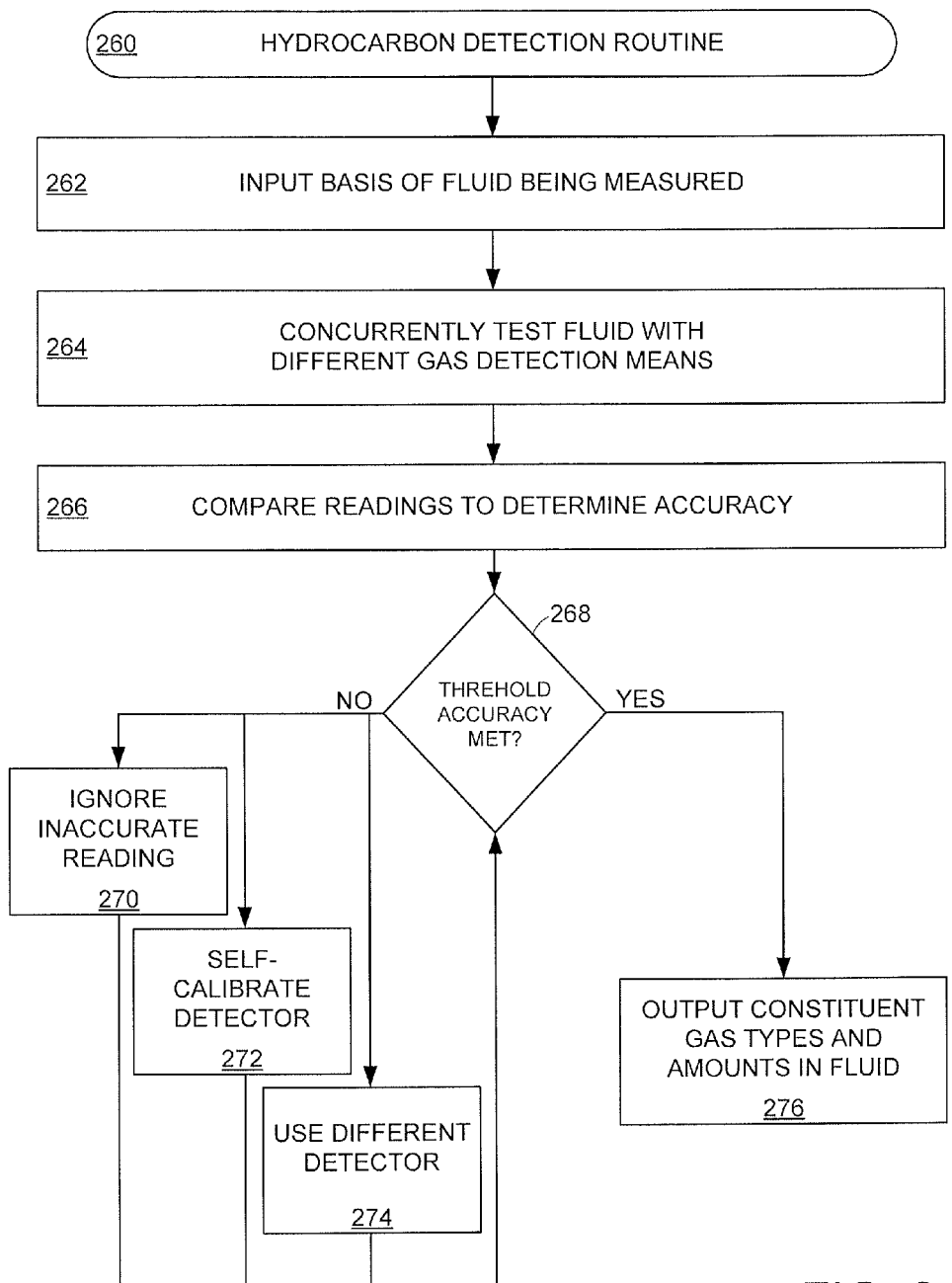
FIG. 8 maps an example hydrocarbon detection routine carried out in accordance with assorted embodiments.

FIG. 8 maps an example hydrocarbon detection routine 260 carried out in accordance with various embodiments without being limiting in any way. Initially, routine 260 can begin with step 262 receiving the basis of the gasses from the fluid being measured, such as water based or oil based fluid. The basis of the fluid to be tested allows the logical algorithm to monitor, calibrate, and adjust the various gas detectors and controlled testing environment to maximize the efficiency and accuracy of gas detection. The calibration of various testing conditions can occur before or during step 264 where fluid is concurrently tested with at least two different gas detection means, such as infrared and thermal coefficient detectors.

Assorted embodiments utilize a multitude of different gas detection means sequentially, individually, and simultaneously per the logical algorithm's direction. That is, the logical algorithm can trigger the activation and deactivation of one or more different gas detection means to maximize testing efficiency and accuracy. As a non-limiting example, a predetermined accuracy threshold, like 95% certainty, can be established prior to or during the testing of a fluid to ensure gas detection results render accuracy above that established threshold. Step 266 compares the logged measurements from the various gas detection means in step 264 to determine a testing accuracy, which can be a range of numbers as well as a specific value.

With the accuracy of the fluid testing determined, decision 268 then evaluates if a predetermined threshold accuracy has been met by the testing conditions of step 264. In the event the threshold accuracy has not been met, an unlimited variety of steps and operations can be undertaken by the gas detection device to provide gas types and amounts contained in the tested fluid with accuracy above the predetermined accuracy threshold. For instance, at least one reading from a gas detection means can be ignored in step 270, which allows results from a malfunctioning or inappropriate gas detection means to not taint results from other gas detection means. Step 270 can be followed by a recalculation of gases constituent in the tested fluid and a comparison of the accuracy of the newly calculated results to the predetermined accuracy threshold back at decision 268.

Either initially or after another operation has failed to meet the threshold accuracy, step 272 can self-calibrate one or more gas detectors. Such self-calibration may take the gas detection means offline or remain online while environmental conditions, such as temperature, humidity, and pressure, are used to compute new gas detection thresholds, which can be conducted passively and without user initiation to provide seamless gas detection. Subsequently, the self-calibrated gas detector can test or retest the fluid to provide more accurate gas detection. However, the return of step 272 to decision 268 indicates that the accuracy of the newly calibrated gas detector is checked against the predetermined threshold accuracy instead of assuming the self-calibration renders a more accuracy gas reading.

Upon failing decision 268, step 274 can alternatively use one or more different gas detectors to increase gas detection accuracy. Step 274 can, in some embodiments, redundantly check for the presence and volume of gases under different conditions like varying pressures and after the gas centrifuge has separated gases. The ability to utilize multiple different corrective steps to increase the accuracy of gas detection allows routine 260 to adapt to changing environmental and fluid conditions to ensure outputted gas results have not been jeopardized by errant, miscalibrated, or inappropriate test detectors.

Regardless of what corrective steps are used to increase the accuracy of gas detection, or in the event no corrective steps are conducted, a gas detection accuracy above the predetermined threshold accuracy advances routine 260 to step 276 where the constituent gas types and amounts for the tested fluid are outputted in real-time. A non-limiting example of such real-time output may be in the form of a running log that is periodically examined, a network stream that is continuously monitored from a remote location, and a datum point that is evaluated by software to provide diagnostic and projected statistics about the fluid and corresponding wellbore in which the fluid was resident.

Through the steps and decision of routine 260, a fluid can be tested with a multitude of different gas detectors before the gas makeup of the fluid is outputted with optimized accuracy. However, the various aspects of routine 260 are not required or limiting as any step and decision can be added, remove, and changed. For example, a step may be added that engages the tested fluid with a gas centrifuge to separate gases prior to step 264 and/or step 274.

The ability to provide a mobile gas detection device can allow fluids to be tested in and in close physical and temporal proximity to their native environments so that constituent gases are not contaminated or lost during transport to a testing facility. The construction of the mobile gas detection device that allows testing of a fluid with multiple different gas detection means individually and concurrently allows a logical algorithm to systematically determine the gas types and amounts present in the fluid with an optimized accuracy. Furthermore, the ability to sense environmental conditions with the mobile gas detection device allows gas detection to adapt to changing environments, such as the harsh and volatile conditions found in hydrocarbon drilling environments.

What is claimed is:

1. A method comprising:
    providing a control module having a plurality of different gas detection means housed in a mobile enclosure;
    activating first and second different gas detection means concurrently with the control module to provide amounts and types of gases present in a mixture of different gasses;
    computing a testing accuracy of the plurality of different gas detection means with the control module;
    conducting a first calibration on a first gas detection means of the plurality of different gas detection means with the control module in response to the testing accuracy being below an accuracy threshold; and
    activating a third gas detection means with the control module in response to the testing accuracy being below the accuracy threshold, the third gas detection means operating concurrently with the second gas detection means.

2. The method of claim 1, wherein the testing accuracy is measured by the control module with a presence of Methane above 1% in the mixture of different gasses.

3. The method of claim 1, wherein the control module measures temperature of the first and second gas detection means to compute the testing accuracy.

4. The method of claim 1, wherein a second calibration on the first gas detection means in response to the control module detecting drifting environmental conditions.

5. The method of claim 1, wherein the control module regulates a voltage of at least one gas detection means.

6. The method of claim 1, wherein a reading measurement from the first gas detection means is ignored by the control module in response to the accuracy threshold not being met.

7. The method of claim 1, wherein the control module measures the testing accuracy by comparing logged measurements from at least a thermal coefficient detector.

8. The method of claim 1, wherein the mixture of different gasses is present in a gas sample and the amounts and types of gases are detected by the plurality of different gas detection means within five minutes of exiting a wellbore.

9. A method comprising:
    providing a control module having a plurality of different gas detection means housed in a mobile enclosure;
    activating different first and second gas detection means concurrently with the control module to provide amounts and types of gases present in a mixture of different gasses;
    computing a testing accuracy of the plurality of different gas detection means with the control module;
    conducting a first calibration on at least one gas detection means in response to an accuracy threshold not being met;
    deactivating the first gas detection means with the control module; and
    activating a third gas detection means with the control module, the third gas detection means operating concurrently with the second gas detection means.

10. The method of claim 9, wherein the second gas detection means remains active while the first gas detection means is deactivated.

11. The method of claim 9, wherein the third gas detection means is activated to increase the testing accuracy of the plurality of different gas detection means.

12. The method of claim 9, wherein the second and third gas detection means are different and sense different types of gasses in the mixture of different gasses.

13. The method of claim 9, wherein the first gas detection means is deactivated in response to a sensor detecting an amount of gas above a predetermined gas threshold.

14. The method of claim 9, wherein a second calibration is conducted on the first gas detection means proactively by the control module.

15. A method comprising:
    providing a control module connected to an oxygen detector, infrared detector, thermal coefficient detector, and pellistor detector, the control module and each detector housed in a mobile enclosure;
    activating the oxygen, infrared, thermal coefficient, and pellistor detectors concurrently with the control module;
    applying one or more algorithms with the control module to provide amounts and types of gases present in a mixture of different gasses based on readings from the oxygen, infrared, thermal coefficient, and pellistor detectors;
    computing a testing accuracy of the plurality of different gas detection means with the control module; and
    conducting a first calibration on at least one detector in response to the testing accuracy being below an accuracy threshold.

16. The method of claim 15, wherein the oxygen detector is ignored until the control module conducts a second calibration on the oxygen sensor and the oxygen detector is certified as accurate by the control module.

17. The method of claim 15, wherein measurements from each detector are averaged to determine the amounts and types of gases.

18. The method of claim 15, wherein the control module conducts a second calibration on at least one detector to detect volatile organic drilling fluid fumes.

19. The method of claim 15, wherein the testing accuracy is below the accuracy threshold due to the mixture of different gasses comprising air not at atmospheric pressure.

* * * * *

UNITED STATES PATENT AND TRADEMARK OFFICE
CERTIFICATE OF CORRECTION

PATENT NO. : 9,903,846 B2
APPLICATION NO. : 14/925572
DATED : February 27, 2018
INVENTOR(S) : Carl Bright Page 1 of 1

It is certified that error appears in the above-identified patent and that said Letters Patent is hereby corrected as shown below:

In the Claims

In Column 15, Line 34: Claim 6:
"wherein a reading measurement" should be "wherein a measurement"

Signed and Sealed this
Seventeenth Day of April, 2018

Andrei Iancu
*Director of the United States Patent and Trademark Office*